(12) United States Patent
Ahmadvand

(10) Patent No.: US 11,786,138 B2
(45) Date of Patent: Oct. 17, 2023

(54) SYSTEM FOR ARTERIAL BLOOD GAS TESTING

(71) Applicant: Omid Ahmadvand, Tehran (IR)

(72) Inventor: Omid Ahmadvand, Tehran (IR)

(*) Notice: Subject to any disclaimer, the term of this patent is extended or adjusted under 35 U.S.C. 154(b) by 214 days.

(21) Appl. No.: 17/207,637

(22) Filed: Mar. 20, 2021

(65) Prior Publication Data

US 2021/0204825 A1    Jul. 8, 2021

Related U.S. Application Data

(60) Provisional application No. 63/035,851, filed on Jun. 8, 2020.

(51) Int. Cl.
*A61B 5/024* (2006.01)
*A61B 5/00* (2006.01)
*A61B 5/15* (2006.01)

(52) U.S. Cl.
CPC ...... *A61B 5/02416* (2013.01); *A61B 5/15003* (2013.01); *A61B 5/702* (2013.01); *A61B 2562/043* (2013.01)

(58) Field of Classification Search
CPC . A61B 5/15003; A61B 5/153; A61B 5/02416; A61B 5/681; A61B 5/68; A61B 5/6824; A61B 2562/043; A61B 2562/063
See application file for complete search history.

(56) References Cited

U.S. PATENT DOCUMENTS

| | | | | |
|---|---|---|---|---|
| 6,132,383 A * | 10/2000 | Chesney | ........ | A61B 5/022 73/866.5 |
| 2017/0105665 A1* | 4/2017 | Ravikumar | ........ | A61B 5/15074 |
| 2018/0177982 A1* | 6/2018 | Albany | ........ | A61B 5/021 |
| 2019/0160231 A1* | 5/2019 | Dobie | ........ | A61M 5/427 |

* cited by examiner

*Primary Examiner* — John Denny Li
(74) *Attorney, Agent, or Firm* — Bajwa IP Law Firm; Haris Zaheer Bajwa

(57) ABSTRACT

A system for facilitating arterial blood gas (ABG) sampling. The system includes a main part, a first plurality of pulse sensors attached in a row on an inner surface of the main part, a first plurality of lights attached in a row on an external surface of the main part, a first opening on the main part adjacent to the first plurality of pulse sensors, and a processor. The processor is configured to receive a first plurality of radial pulse intensities from the first plurality of pulse sensors, determine a highest radial pulse intensity among the first plurality of radial pulse intensities, and turn on a light from the first plurality of lights associated with the highest pulse intensity among the first plurality of radial pulse intensities.

2 Claims, 13 Drawing Sheets

102

SYSTEM FOR ARTERIAL BLOOD GAS TESTING

CROSS-REFERENCE TO RELATED APPLICATION

This application claims the benefit of priority from U.S. Provisional Patent Application Ser. No. 63/035,851, filed on Jun. 8, 2020, and entitled "FACILITATOR FOR SAMPLING ARTERIAL BLOOD GAS" which is incorporated herein by reference in its entirety.

TECHNICAL FIELD

This disclosure relates to blood tests, and particularly relates to arterial blood gas (ABG) testing. More particularly, the present disclosure relates to a system for facilitating arterial blood gas testing.

BACKGROUND

A blood gas test is generally used to measure the amounts of oxygen and carbon dioxide in the blood and determine the acidity of the blood. The blood gas test is also commonly referred to as arterial blood gas analysis. Unlike most typical blood tests, for which samples are drawn from a vein, the blood gases sample is generally taken from an artery, usually in the wrist, groin, or arm. First, the site of the venipuncture may be cleaned and disinfected. Then, a local anesthetic may be injected. Once the area is numb, a needle may be inserted into the artery and a sample of blood may be withdrawn into a special syringe that may prevent any contamination by outside air. After the sample is drawn into the syringe, pressure may be applied to the site for about 5 to 15 minutes to prevent bleeding.

Blood gas measurements, performed by trained personnel, are usually carried out in a hospital, emergency room, or large laboratory setting. The analysis may be done immediately following sample collection and specialized equipment may be required. Since the blood sample is taken from the artery, a patient undergoing a traditional arterial blood gas test, may experience more pain and discomfort than other blood tests that instead utilize venous blood samples. There is, therefore, a need for a system that help a sampler to perform a non-invasive blood gas test that is less painful to the patients, is safe for the patients, and generates fast results.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one or more exemplary embodiments, the present disclosure is directed to a system for facilitating arterial blood gas (ABG) sampling. In an exemplary embodiment, the system may include a main part, a first plurality of pulse sensors, a first plurality of lights, a first opening, and a processor.

In an exemplary embodiment, the main part may be configured to be secured on a palm side of a user's wrist. In an exemplary embodiment, the first plurality of sensors may be attached in a row on an inner surface of the main part. In an exemplary embodiment, each pulse sensor from the first plurality of pulse sensors may be configured to measure an intensity of radial pulse around the each pulse sensor.

In an exemplary embodiment, the first plurality of lights may be attached in a row on an external surface of the main part. In an exemplary embodiment, each respective light from the first plurality of lights may be associated with a respective pulse sensor from the first plurality of pulse sensors. In an exemplary embodiment, the first opening may be provided on the main part adjacent to the first plurality of pulse sensors.

In an exemplary embodiment, the first opening may be configured to allow access to a skin of the user's wrist for a sampler. In an exemplary embodiment, the first opening may further be configured to receive a sampling needle and pass the sampling needle through the first opening to the skin of the user's wrist.

In an exemplary embodiment, the processor may be configured to receive a first plurality of radial pulse intensities from the first plurality of pulse sensors. In an exemplary embodiment, each radial pulse intensity from the first plurality of radial pulse intensities may be associated with a respective pulse sensor from the first plurality of pulse sensors.

In an exemplary embodiment, the processor may also be configured to determine a highest radial pulse intensity among the first plurality of radial pulse intensities. In an exemplary embodiment, the processor may further be configured to turn on a light from the first plurality of lights associated with the highest pulse intensity among the first plurality of radial pulse intensities. In an exemplary embodiment, each light from the first plurality of lights may be placed behind a respective pulse sensor from the first plurality of pulse sensors.

In an exemplary embodiment, the system may further include a second plurality of pulse sensors and a second plurality of lights. In an exemplary embodiment, the second plurality of pulse sensors may be attached in a row on the internal surface of the main part. In an exemplary embodiment, each pulse sensor from the second plurality of pulse sensors may be configured to measure an intensity of radial pulse around each respective pulse sensor.

In an exemplary embodiment, the second plurality of lights may be attached in a row on the external surface of the main part. In an exemplary embodiment, each respective light from the second plurality of lights may be associated with a respective pulse sensor from the second plurality of pulse sensors.

In an exemplary embodiment, the first opening may be placed between the first plurality of pulse sensors and the second plurality of pulse sensors. In an exemplary embodiment, the processor may further be configured to receive a second plurality of radial pulse intensities from the second plurality of pulse sensors. In an exemplary embodiment, each respective radial pulse intensity from the second plurality of radial pulse intensities associated with a respective pulse sensor from the second plurality of pulse sensors.

In an exemplary embodiment, the processor may further be configured to determine a highest radial pulse intensity among the second plurality of radial pulse intensities. In an exemplary embodiment, the processor may also be configured to turn on a light from the second plurality of lights associated with the highest radial pulse intensity among the second plurality of radial pulse intensities. In an exemplary embodiment, each light from the second plurality of lights is placed behind a respective pulse sensor from the second plurality of pulse sensors.

In an exemplary embodiment, the system may further include a third plurality of pulse sensors, a third plurality of lights, and a second opening. In an exemplary embodiment, the third plurality of pulse sensors may be attached in a row on the internal surface of the main part. In an exemplary embodiment, each pulse sensor from the third plurality of pulse sensors may be configured to measure an intensity of radial pulse around the each pulse sensor.

In an exemplary embodiment, the third plurality of lights may be attached in a row on the external surface of the main part. In an exemplary embodiment, each respective light from the third plurality of lights may be associated with a respective pulse sensor from the third plurality of pulse sensors. In an exemplary embodiment, the second opening may be provided on the main part between the second plurality of pulse sensors and the third plurality of pulse sensors.

In an exemplary embodiment, the second opening may be configured to allow access to the skin of the user's wrist for a sampler. In an exemplary embodiment, the second opening may be configured to receive the sampling needle and pass the sampling needle through the second opening to the skin of the user's wrist.

In an exemplary embodiment, the processor may further be configured to receive a third plurality of radial pulse intensities from the third plurality of pulse sensors. In an exemplary embodiment, each respective radial pulse intensity from the third plurality of radial pulse intensities may be associated with a respective pulse sensor from the third plurality of pulse sensors. The processor may also be configured to determine a highest radial pulse intensity among the third plurality of radial pulse intensities and turn on a light from the third plurality of lights associated with the highest radial pulse intensity among the third plurality of radial pulse intensities.

In an exemplary embodiment, the first plurality of pulse sensors may be equally spaced on the inner surface of the main part. In an exemplary embodiment, the first plurality of lights may be equally spaced on the external surface of the main part. In an exemplary embodiment, the second plurality of pulse sensors may be equally spaced on the inner surface of the main part. In an exemplary embodiment, the second plurality of lights may be equally spaced on the external surface of the main part. In an exemplary embodiment, the third plurality of pulse sensors may be equally spaced on the inner surface of the main part. In an exemplary embodiment, the third plurality of lights may be equally spaced on the external surface of the main part.

In an exemplary embodiment, a first light from the first plurality of lights may be placed adjacent to a first end of the first opening. In an exemplary embodiment, a second light from the first plurality of lights may be placed adjacent to a second end of the first opening. In an exemplary embodiment, a first light from the second plurality of lights may be placed adjacent to the first end of the first opening and a first end of the second opening. In an exemplary embodiment, a second light from the second plurality of lights may be placed adjacent to the second end of the first opening and a second end of the second opening. In an exemplary embodiment, a first light from the third plurality of lights may be placed adjacent to the first end of the second opening. In an exemplary embodiment, a second light from the third plurality of lights may be placed adjacent to the second end of the second opening.

In an exemplary embodiment, each light from the third plurality of lights may be placed behind a respective pulse sensor from the third plurality of pulse sensors. In an exemplary embodiment, the system may further include a wrist gripping member. In an exemplary embodiment, the wrist gripping member may be configured to receive the user's wrist and hold and secure the user's wrist in a predetermined position.

In an exemplary embodiment, the system may further include a first wristlet band and a second wristlet band. In an exemplary embodiment, the first wristlet band may be attached to a first end of the main part. In an exemplary embodiment, the second wristlet band may be attached to a second end of the main part. In an exemplary embodiment, the first wristlet band and the second wristlet band may be configured to secure the main part on the palm side of the user's wrist.

In an exemplary embodiment, the wrist gripping member may include a cushion part configured to receive and hold a forearm of the user. In an exemplary embodiment, the wrist gripping member may further include an inclined hand holding part. In an exemplary embodiment, a proximal end of the inclined hand holding part may be attached to a distal end of the cushion part. In an exemplary embodiment, the inclined hand holding part may be configured to receive and hold a hand of the user.

In an exemplary embodiment, the cushion part and the inclined hand holding part may form an angle between the cushion part and the inclined hand holding part. In an exemplary embodiment, the angle may be between 120° and 160°. In an exemplary embodiment, the system may further include a hand gripping band attached to a back side of the inclined hand holding part. In an exemplary embodiment, the hand gripping band may be configured to secure a hand of the user on the inclined hand holding part.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
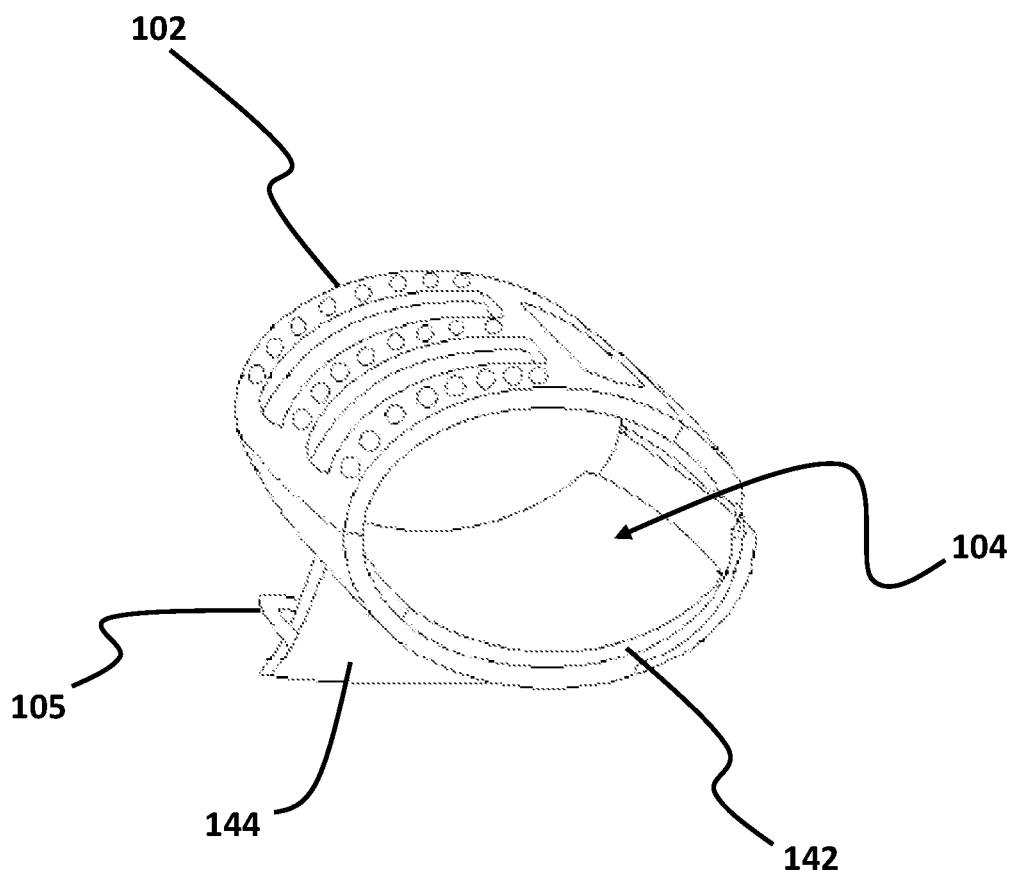
FIG. 1A illustrates a perspective view of a system 100 for facilitating arterial blood gas (ABG) sampling, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary system for facilitating arterial blood gas testing. An exemplary system may include a main part which may be able to be secured on a palm side of a user's wrist. The system may include a first row of pulse sensors, a second row of pulse sensors, and a third row of pulse sensors on an inner surface of the main part. The system may also include a first row of lights, a second row of lights, and a third row of lights on an outer surface of the main part. Each light from the first row of lights may be placed behind a respective pulse sensor from the first row of pulse sensors. Each light from the second row of lights may be placed behind a respective pulse sensor from the second row of pulse sensors. Each light from the third row of lights may be placed behind a respective pulse sensor from the third row of pulse sensors. Each of the pulse sensors may measure an intensity of radial pulse around. A processor may detect the highest radial pulse intensity in each row and turn on a light which may be placed behind the pulse sensor which measures the biggest radial pulse intensity.

The system may further include a first opening between the first row of lights and the second row of lights and a second opening between the second row of lights and the third row of lights. A sampler may choose a point in one of the openings from the first opening or the second opening for inserting a sampling needle to a skin of a user's wrist. In an exemplary embodiment, on lights on first row of lights, second row of lights, and third row of lights may be indications for an artery of a user. A sampler may be able to find a right place for inserting the sampling needle more easily.

Figure 1B:
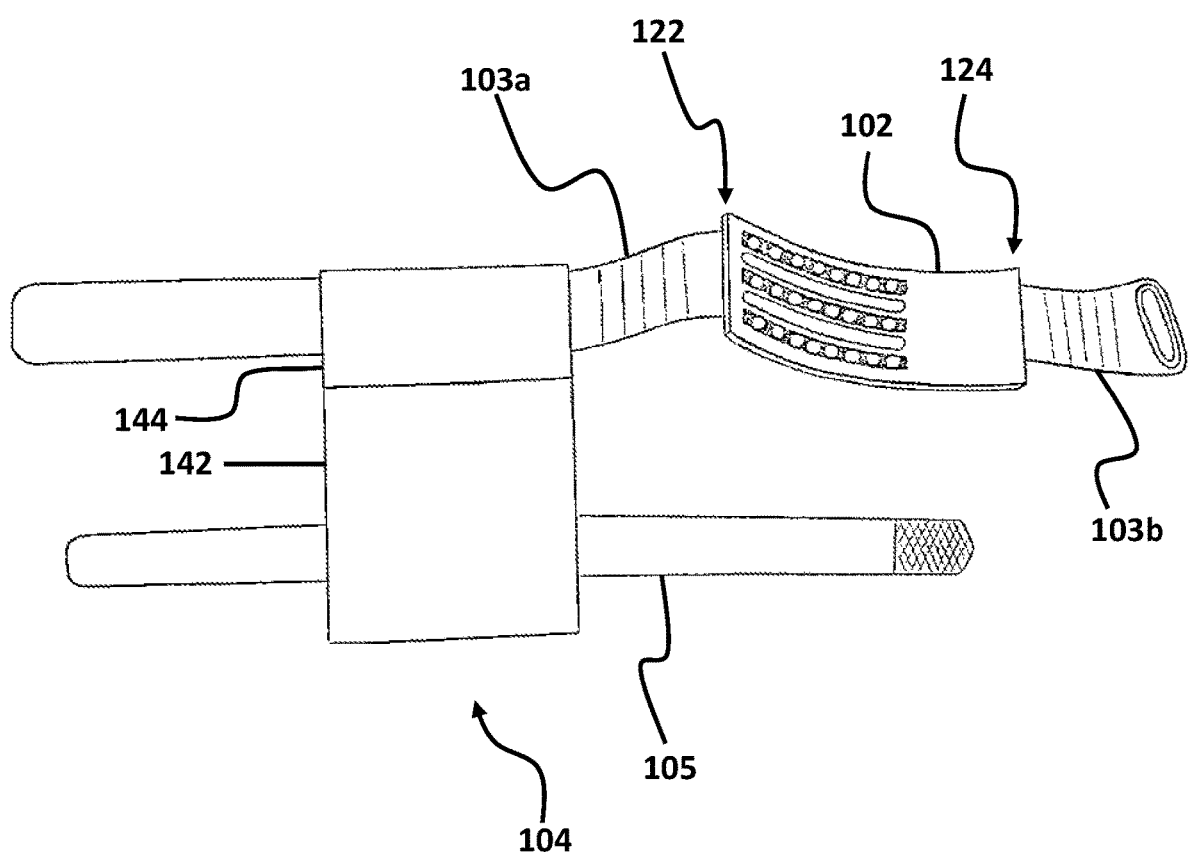
FIG. 1B illustrates an open view of a system, consistent with one or more exemplary embodiments of the present disclosure.
Figure 1C:
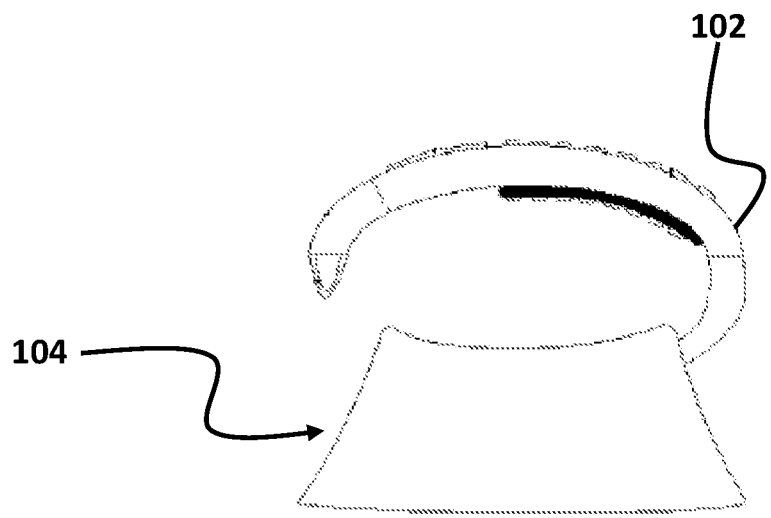
FIG. 1C illustrates a front view of a system, consistent with one or more exemplary embodiments of the present disclosure.
Figure 1D:
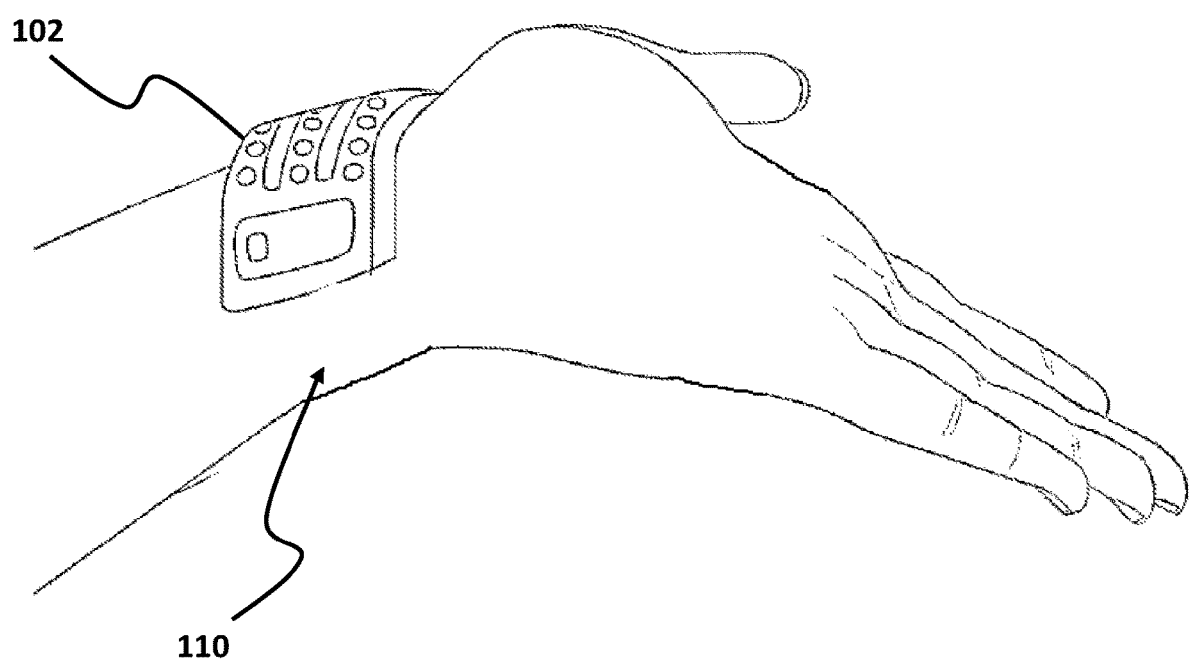

FIG. 1A shows a perspective view of a system 100 for facilitating arterial blood gas (ABG) sampling, consistent with one or more exemplary embodiments of the present disclosure. FIG. 1B shows an open view of system 100, consistent with one or more exemplary embodiments of the present disclosure. FIG. 1C shows a front view of system 100, consistent with one or more exemplary embodiments of the present disclosure. As shown in FIG. 1A and FIG. 1B, in an exemplary embodiment, system 100 may include a main part 102. In an exemplary embodiment, main part 102 may be configured to be secured on a palm side of a user's wrist. In an exemplary embodiment, system 100 may further include a first wristlet band 103a and a second wristlet band 103b. In an exemplary embodiment, first wristlet band 103a may be attached to a first end 122 of main part 102. In an exemplary embodiment, second wristlet band 103b may be attached to a second end 124 of main part 102. In an exemplary embodiment, first wristlet band 103a and second wristlet band 103b may be configured to secure main part 102 on a palm side of a user's wrist. In an exemplary embodiment, main part 102 may have a curved shape coinciding with a curved shape of a palm side of a user's wrist. FIG. 1D shows main part 102 when main part 102 is secured on a palm side of a user's wrist, consistent with one or more exemplary embodiments of the present disclosure. As shown in FIG. 1D, in an exemplary embodiment, main part 102 may have a curved shape. In an exemplary embodiment, the curved shape may coincide with a curved shape of a palm side of a user's wrist 110.

Figure 2A:
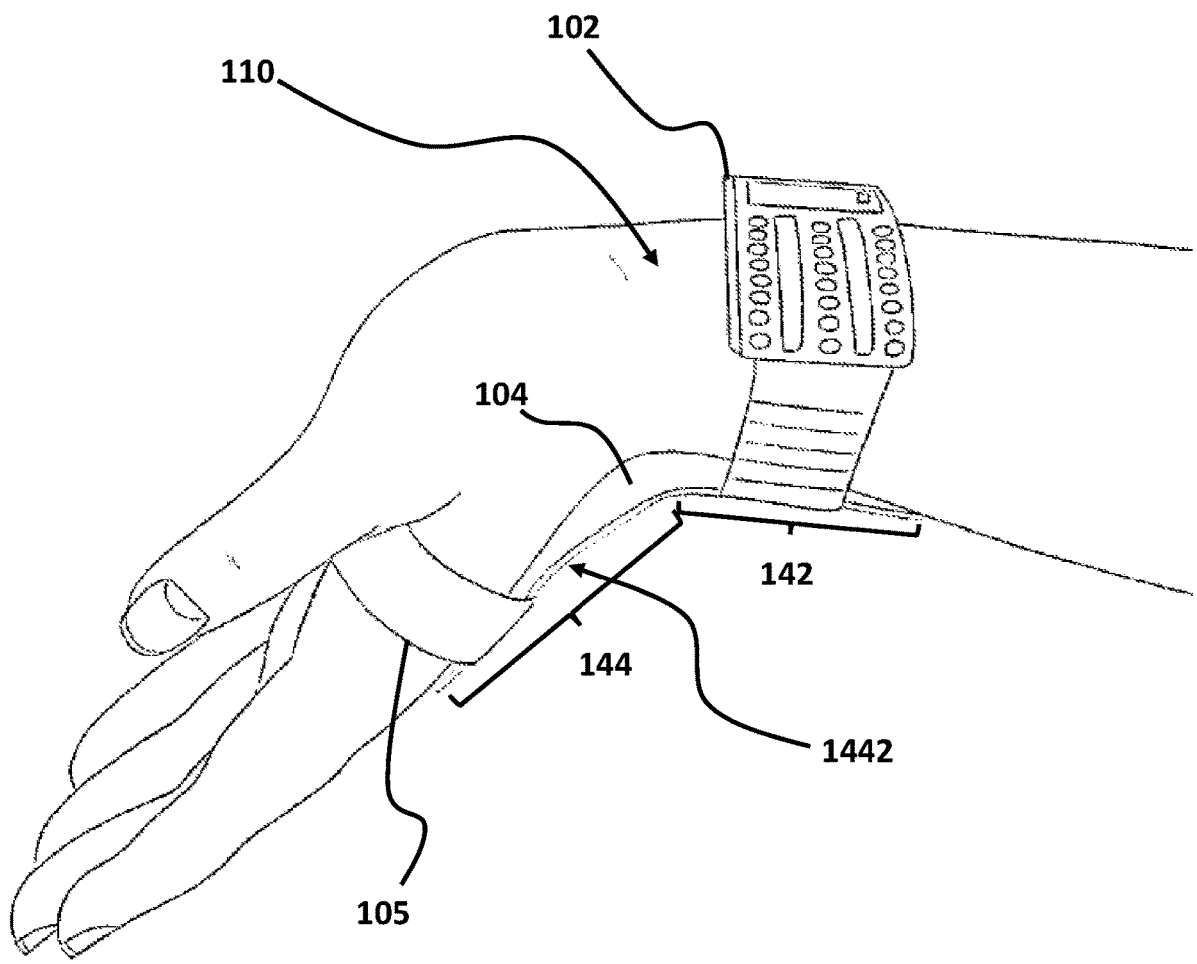
FIG. 2A illustrates a system in a scenario in which a user's wrist is inserted into a wrist gripping member, consistent with one or more exemplary embodiments of the present disclosure.
Figure 2B:
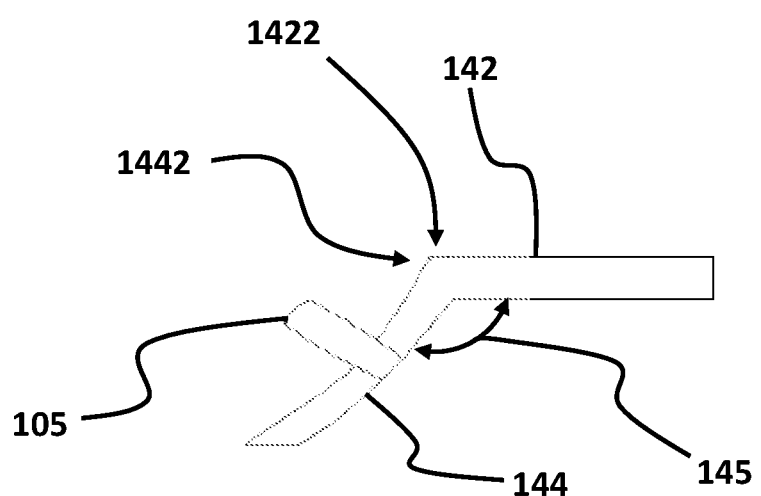
FIG. 2B illustrates a side view of a wrist gripping member, consistent with one or more exemplary embodiments of the present disclosure.
Figure 2C:
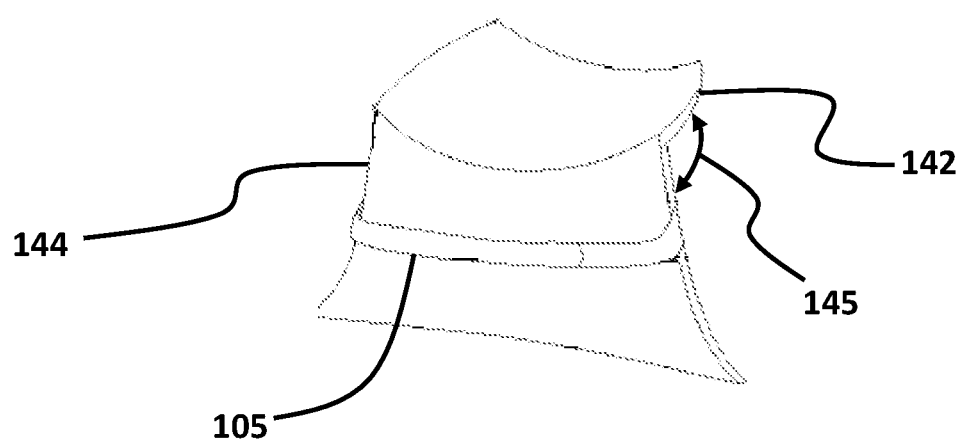
FIG. 2C illustrates a perspective view of a wrist gripping member, consistent with one or more exemplary embodiments of the present disclosure.

In an exemplary embodiment, system 100 may further include a wrist gripping member 104. In an exemplary embodiment, wrist gripping member 104 may be configured to receive or hold a wrist such as user's wrist 110 and secure the wrist such as user's wrist 110 in a predetermined position. FIG. 2A shows system 100 in a scenario in which user's wrist 110 is inserted into wrist gripping member 104, consistent with one or more exemplary embodiments of the present disclosure. FIG. 2B shows a side view of wrist gripping member 104, consistent with one or more exemplary embodiments of the present disclosure. FIG. 2C shows a perspective view of wrist gripping member 104, consistent with one or more exemplary embodiments of the present disclosure. As shown in FIG. 2B and FIG. 2C, in an exemplary embodiment, wrist gripping member 104 may include a cushion part 142 and an inclined hand holding part 144.

In an exemplary embodiment, cushion part 142 may be configured to receive and hold a forearm of a user as shown in FIG. 2A. In an exemplary embodiment, inclined hand holding part 144 may be configured to receive and hold a hand of a user as shown in FIG. 2A. In an exemplary embodiment, a proximal end 1442 of inclined hand holding part 144 may be attached to a distal end 1422 of cushion part 142. In an exemplary embodiment, cushion part 142 and hand holding part 144 may define a wrist angle 145 between proximal end 1442 of inclined hand holding part 144 and distal end 1422 of cushion part 142. In an exemplary embodiment, wrist angle 145 may be between 120° and 160°. In an exemplary embodiment, wrist angle 145 may be 145°.

Figure 2D:
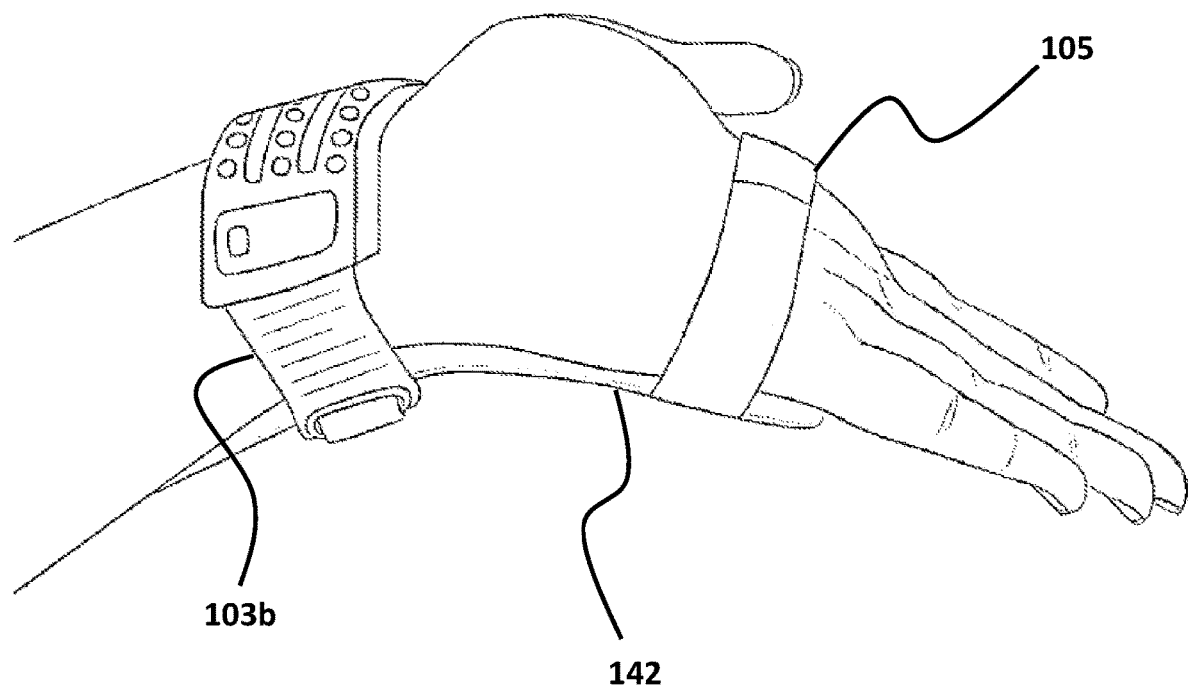
FIG. 2D illustrates a system in a scenario in which a hand of a user is placed on an inclined hand holding part and a hand gripping band is wrapped around the hand of the user, consistent with one or more exemplary embodiments of the present disclosure.

In an exemplary embodiment, system 100 may further include a hand gripping band 105. In an exemplary embodiment, hand gripping band 105 may be attached to a back surface 1442 of inclined hand holding part 144. In an exemplary embodiment, after that a hand of a user is placed onto inclined hand holding part 144, hand gripping band 105 may be used to secure the hand of the user at place. In an exemplary embodiment, after that a hand of a user is placed onto inclined hand holding part 144, hand gripping band 105 may be wrapped around the hand of the user to tightly grip the hand. FIG. 2D shows system 100 in a scenario in which a hand of a user is placed on inclined hand holding part 144 and hand gripping band 105 is wrapped around the hand of the user, consistent with one or more exemplary embodiments of the present disclosure.

Figure 3A:
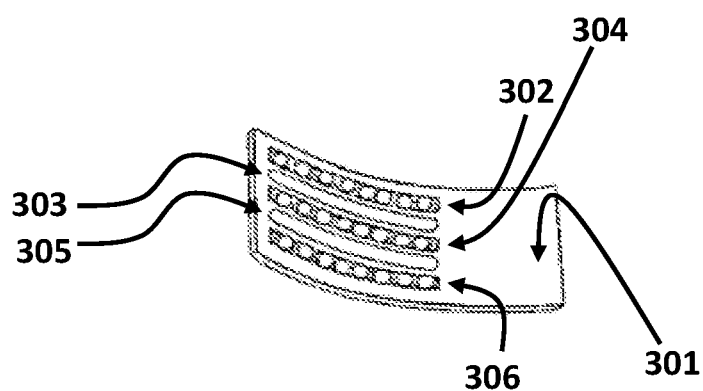
FIG. 3A illustrates a bottom view of a main part, consistent with one or more exemplary embodiments of the present disclosure.

FIG. 3A shows a bottom view of main part 102, consistent with one or more exemplary embodiments of the present disclosure. As shown un FIG. 3A, in an exemplary embodiment, system 100 may further include a first plurality of pulse sensors 302, a second plurality of pulse sensors 304, and a third plurality of pulse sensors 306. In an exemplary embodiment, first plurality of pulse sensors 302, second plurality of pulse sensors 304, and third plurality of pulse sensors 306 may be attached to an inner surface 301 of main part 102. In an exemplary embodiment, first plurality of pulse sensors 302 may be attached in a first row on an inner surface 301 of main part 102. In an exemplary embodiment, second plurality of pulse sensors 304 may be attached in a second row on an inner surface 301 of main part 102. In an exemplary embodiment, third plurality of pulse sensors 306 may be attached in a third row on an inner surface 301 of main part 102. In an exemplary embodiment, each pulse sensor from first plurality of pulse sensors 302, second plurality of pulse sensors 304, and third plurality of pulse sensors 306 may measure an intensity of radial pulse around each respective pulse sensor.

Figure 3B:
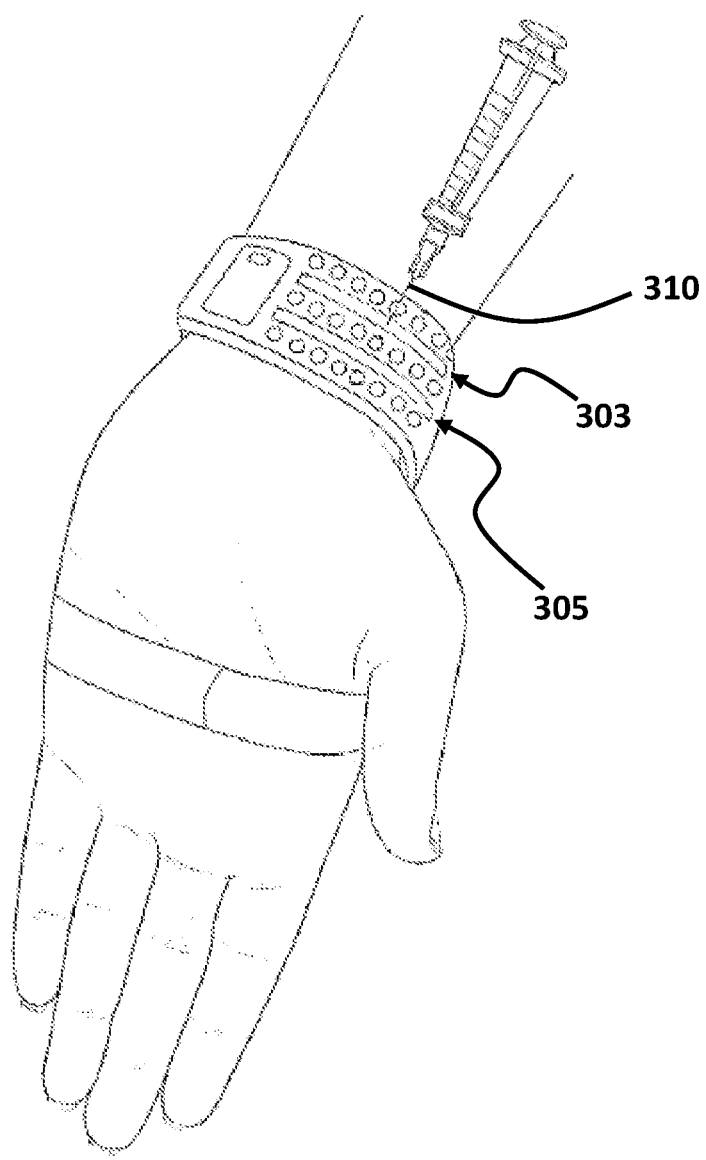
FIG. 3B illustrates a main part secured on a user's wrist, consistent with one or more exemplary embodiments of the present disclosure.

In an exemplary embodiment, system 100 may further include a first opening 303 and a second opening 305. In an exemplary embodiment, first opening 303 may be between first plurality of pulse sensors 302 and second plurality of pulse sensors 304. In an exemplary embodiment, second opening 305 may be between second plurality of pulse sensors 304 and third plurality of pulse sensors 306. In an exemplary embodiment, first opening 303 and second opening 305 may allow passage and access to a skin of a user's wrist. In an exemplary embodiment, first opening 303 and second opening 305 may be configured to receive a sampling needle. FIG. 3B shows main part 102 secured on a user's wrist, consistent with one or more exemplary embodiments of the present disclosure. For example, as shown in FIG. 3B, second opening 303 may allow passage and access to a skin of a user's wrist and receive a sampling needle 310.

Figure 3C:
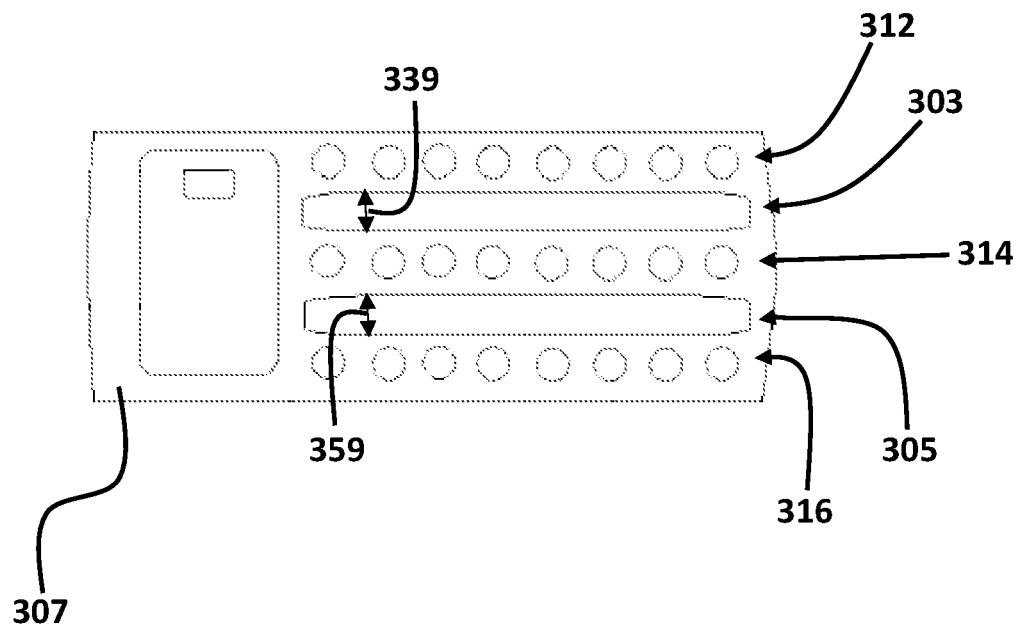
FIG. 3C illustrates a top view of a main part, consistent with one or more exemplary embodiments of the present disclosure.

FIG. 3C shows a top view of main part 102, consistent with one or more exemplary embodiments of the present disclosure. As shown in FIG. 3C, in an exemplary embodiment, system 100 may further include a first plurality of lights 312, a second plurality of lights 314, and a third plurality of lights 316. In an exemplary embodiment, first plurality of lights 312 may be attached in a fourth row on an outer surface 307 of main part 102. In an exemplary embodiment, second plurality of lights 314 may be attached in a fifth row on outer surface 307 of main part 102. In an exemplary embodiment, third plurality of lights 316 may be attached in a sixth row on outer surface 307 of main part 102.

In an exemplary embodiment, each light from first plurality of lights 312 may be associated with a respective pulse sensor from first plurality of pulse sensors 302. In an exemplary embodiment, each light from first plurality of lights 312 may be placed behind a respective pulse sensor from first plurality of pulse sensors 302. In an exemplary embodiment, each light from second plurality of lights 314 may be associated with a respective pulse sensor from second plurality of pulse sensors 304. In an exemplary embodiment, each light from second plurality of lights 314 may be placed behind a respective pulse sensor from second plurality of pulse sensors 304. In an exemplary embodiment, each light from third plurality of lights 316 may be associated with a respective pulse sensor from third plurality of pulse sensors 306. In an exemplary embodiment, each light from third plurality of lights 316 may be placed behind a respective pulse sensor from third plurality of pulse sensors 306. In an exemplary embodiment, when a light is placed behind a pulse sensor, it may mean that the light and the pulse sensor are attached on opposite sides of main part 102 in such a way that an interconnecting line between the light and the pulse sensor is perpendicular to a tangential surface of main part 102 which passes through a common point of main part 102 and the interconnecting line between the light and the pulse sensor.

In an exemplary embodiment, a distance between each two consecutive lights from first plurality of lights 312, second plurality of lights 314, and third plurality of lights 316 may be 5 mm. In an exemplary embodiment, a distance between centers of each two consecutive pulse sensors from first plurality of pulse sensors 302, second plurality of pulse sensors 304, and third plurality of pulse sensors 306 may be 5 mm. In an exemplary embodiment, a width 339 of first opening 303 may be 4 mm. In an exemplary embodiment, a width 359 of second opening 305 may be 4 mm.

Figure 3D:
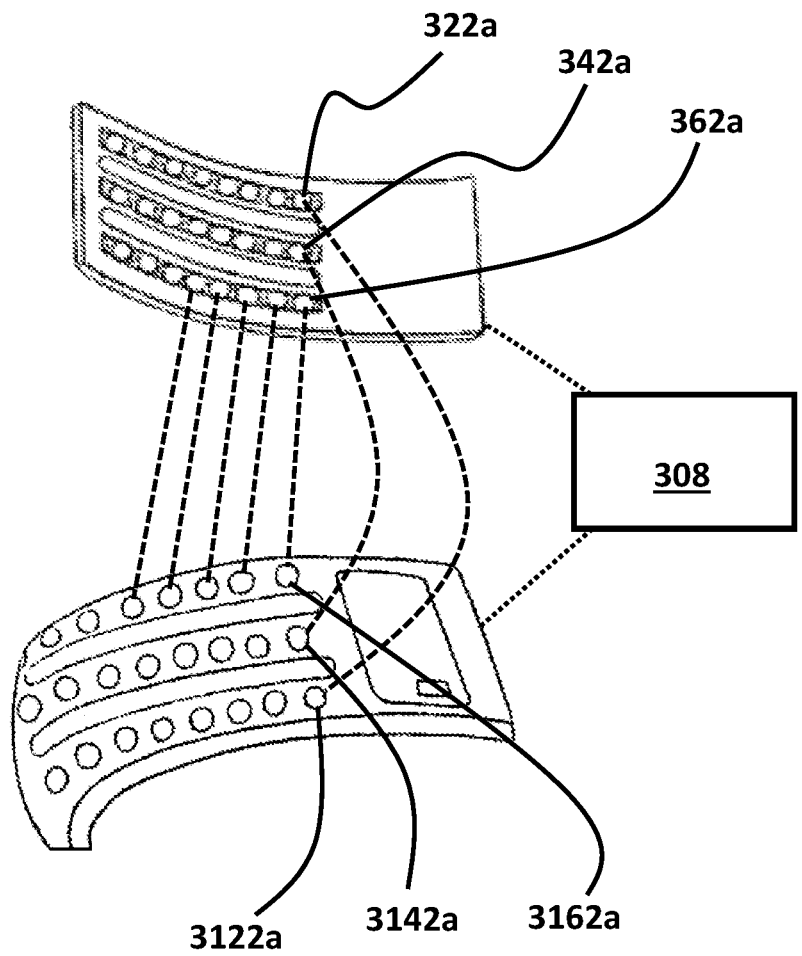
FIG. 3D illustrates a top view and a bottom view of a main part, consistent with one or more exemplary embodiments of the present disclosure.

FIG. 3D shows a top view and a bottom view of main part 102, consistent with one or more exemplary embodiments of the present disclosure. In an exemplary embodiment, a first pulse sensor 322*a* from first plurality of pulse sensors 302 may be behind a first light 3122*a* from first plurality of lights 312. In an exemplary embodiment, a second pulse sensor 342*a* from second plurality of pulse sensors 304 may be behind a second light 3142*a* from second plurality of lights 314. In an exemplary embodiment, a third pulse sensor 362*a* from third plurality of pulse sensors 306 may be behind a third light 3162*a* from third plurality of lights 316.

As shown in FIG. 3D, in an exemplary embodiment, system 100 may further include a processor 308. In an exemplary embodiment, processor 308 may receive a first plurality of radial pulse intensities from first plurality of pulse sensors 302, receive a second plurality of radial pulse intensities from second plurality of pulse sensors 304, and receive a third plurality of radial pulse intensities from third plurality of pulse sensors 306. In an exemplary embodiment, each radial pulse intensity from the first plurality of radial pulse intensities may be measured utilizing a respective pulse sensor from first plurality of pulse sensors 302. For example, first radial pulse intensity from the first plurality of radial pulse intensities may be measured utilizing first pulse sensor 322*a*. In an exemplary embodiment, each radial pulse intensity from the second plurality of radial pulse intensities may be measured utilizing a respective pulse sensor from second plurality of pulse sensors 304. For example, second radial pulse intensity from the second plurality of radial pulse intensities may be measured utilizing second pulse sensor 342a. In an exemplary embodiment, each radial pulse intensity from the third plurality of radial pulse intensities may be measured utilizing a respective pulse sensor from third plurality of pulse sensors 306. For example, third radial pulse intensity from the third plurality of radial pulse intensities may be measured utilizing third pulse sensor 362a.

In an exemplary embodiment, processor 308 may further determine a first highest radial pulse intensity among the first plurality of radial pulse intensities and turn on a light from first plurality of lights 312 associated with the first highest radial pulse intensity. In an exemplary embodiment, the on light may be an indicator for the first highest radial pulse intensity among the first plurality of radial pulse intensities. In an exemplary embodiment, when a sampler sees that a light from first plurality of lights 312 is on, the sampler may understand that the pulse sensor which is located behind the on light has the highest radial pulse intensity among first plurality of pulse sensors 302. In an exemplary embodiment, the first highest radial pulse intensity may be the highest radial pulse intensity among the first plurality of radial pulse intensities. In an exemplary embodiment, processor 308 may further determine a second highest radial pulse intensity among the second plurality of radial pulse intensities and turn on a light from second plurality of lights 314 associated with the second highest radial pulse intensity. In an exemplary embodiment, the second highest radial pulse intensity may be the highest radial pulse intensity among the second plurality of radial pulse intensities. In an exemplary embodiment, processor 308 may further determine a third highest radial pulse intensity among the third plurality of radial pulse intensities and turn on a light from third plurality of lights 316 associated with the third highest radial pulse intensity. In an exemplary embodiment, the third highest radial pulse intensity may be the highest radial pulse intensity among the third plurality of radial pulse intensities.

For example, in a scenario that the first highest radial pulse intensity is measured by first pulse sensor 322a, processor 308 may turn on first light 3122a which may be located behind first pulse sensor 322a. Similarly, in a scenario that the second highest radial pulse intensity is measured by second pulse sensor 342a, processor 308 may turn on second light 3142a which may be located behind second pulse sensor 342a. For another example, in a scenario that the third highest radial pulse intensity is measured by third pulse sensor 362a, processor 308 may turn on third light 3162a which may be located behind third pulse sensor 362a. In an exemplary embodiment, when a light from first plurality of lights 312 is turned on, it may be understood that the first highest radial pulse intensity is measured by a pulse sensor from first plurality of pulse sensors 302 which may be located behind the on light. In an exemplary embodiment, when a light from second plurality of lights 314 is turned on, it may be understood that the second highest radial pulse intensity is measured by a pulse sensor from second plurality of pulse sensors 304 which is located behind the on light. In an exemplary embodiment, when a light from third plurality of lights 316 is turned on, it may be understood that the third highest radial pulse intensity is measured by a pulse sensor from third plurality of pulse sensors 306 which is located behind the on light.

In an exemplary, it may be understood that when a light from first plurality of lights 312, a light from second plurality of lights 314, and a light from third plurality of lights 316 are turned on, a sampler may more easily choose a point on a skin of a user's wrist to insert sampling needle 310 for taking a sample from an artery of the user. In an exemplary embodiment, system 100 may be utilized to effectively find an exemplary artery because radial pulse intensity may be more intense around an artery of a user so the on lights may help a sampler to estimate a location of an artery of a user on his or her wrist and choose a location along first opening 303 or second opening 305 to insert a sampling needle into the user's wrist skin.

Figure 3E:
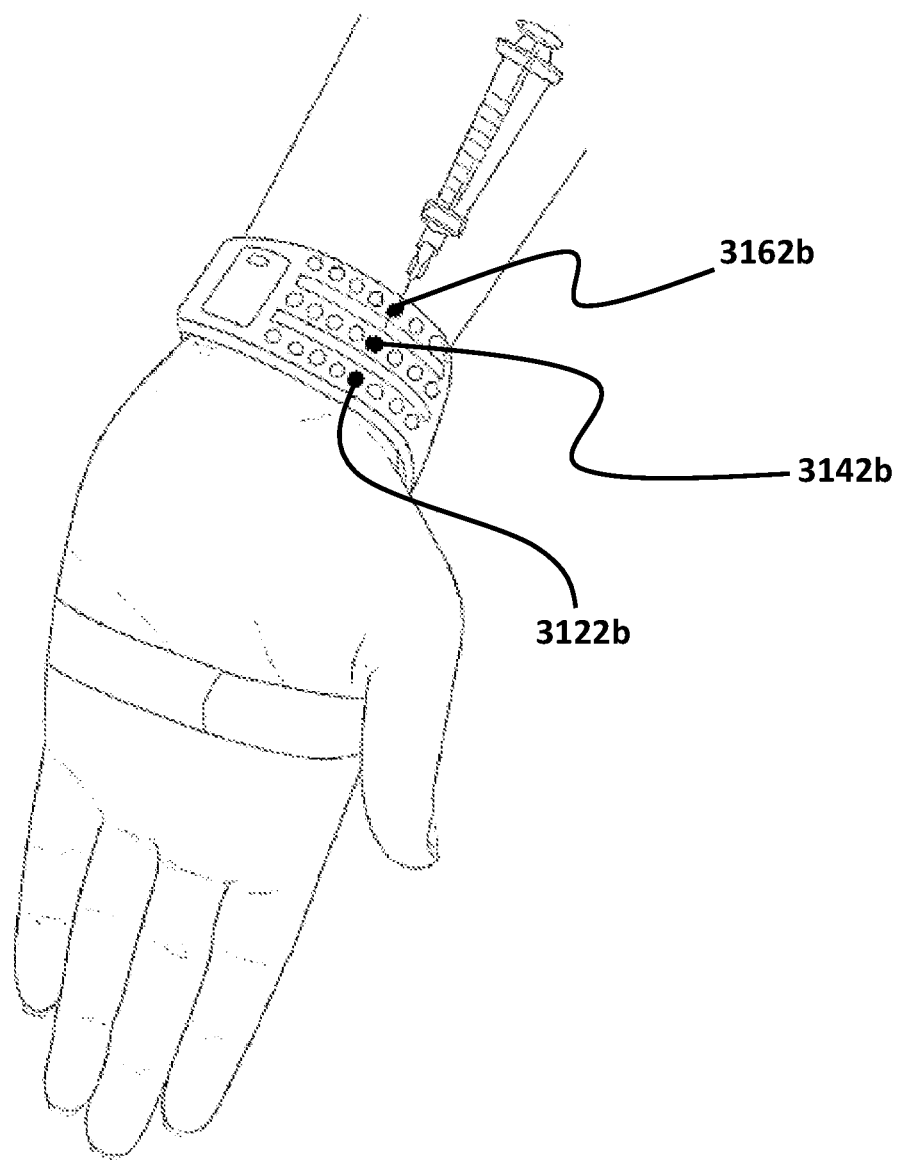
FIG. 3E illustrates a main part secured on a user's wrist, consistent with one or more exemplary embodiments of the present disclosure.

FIG. 3E shows main part 102 secured on a user's wrist, consistent with one or more exemplary embodiments of the present disclosure. As shown in FIG. 3E, for example, a fourth light 3122a from first plurality of lights 312, a fifth light 3142a from second plurality of lights 314, and a sixth light 3162a from third plurality of lights 316 may be turned on. In an exemplary embodiment, based on the on lights, a sampler may choose a point on a skin of a user's wrist to insert sampling needle 310 for taking a sample from an artery of the user.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective spaces of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for facilitating arterial blood gas (ABG) sampling, the system comprising:
    a main part configured to be secured on a palm side of a user's wrist;
    a first plurality of pulse sensors attached in a row on an inner surface of the main part, each pulse sensor from the first plurality of pulse sensors configured to measure an intensity of radial pulse around the each pulse sensor, the first plurality of pulse sensors equally spaced on the inner surface of the main part;
    a first plurality of lights attached in a row on an external surface of the main part, each respective light from the first plurality of lights associated with a respective pulse sensor from the first plurality of pulse sensors, each light from the first plurality of lights placed behind a respective pulse sensor from the first plurality of pulse sensors, the first plurality of lights equally spaced on the external surface of the main part;
    a second plurality of pulse sensors attached in a row on the internal surface of the main part, each pulse sensor from the second plurality of pulse sensors configured to measure an intensity of radial pulse around each respective pulse sensor, the second plurality of pulse sensors equally spaced on the inner surface of the main part;
    a second plurality of lights attached in a row on the external surface of the main part, each respective light from the second plurality of lights associated with a respective pulse sensor from the second plurality of pulse sensors, each light from the second plurality of lights placed behind a respective pulse sensor from the second plurality of pulse sensors, the second plurality of lights equally spaced on the external surface of the main part;
    a third plurality of pulse sensors attached in a row on the internal surface of the main part, each pulse sensor from the third plurality of pulse sensors configured to measure an intensity of radial pulse around the each pulse sensor, the third plurality of pulse sensors equally spaced on the inner surface of the main part;
    a third plurality of lights attached in a row on the external surface of the main part, each respective light from the third plurality of lights associated with a respective pulse sensor from the second plurality of pulse sensors, each light from the third plurality of lights placed behind a respective pulse sensor from the third plurality of pulse sensors, the third plurality of lights equally spaced on the external surface of the main part;
    a first opening on the main part adjacent to the first plurality of pulse sensors, the first opening placed between the first plurality of pulse sensors and the second plurality of pulse sensors, a first light from the first plurality of lights placed adjacent to a first end of the first opening, a second light from the first plurality of lights placed adjacent to a second end of the first opening, the first opening configured to:
        allow access to a skin of the user's wrist for a sampler; and
        receive a sampling needle and pass the sampling needle through the first opening to the skin of the user's wrist;
    a second opening on the main part between the second plurality of pulse sensors and the third plurality of pulse sensors, a first light from the second plurality of lights placed adjacent to the first end of the first opening and a first end of the second opening, a second light from the second plurality of lights placed adjacent to the second end of the first opening and a second end of the second opening, a first light from the third plurality of lights placed adjacent to the first end of the second opening, a second light from the third plurality of lights placed adjacent to the second end of the second opening, the second opening configured to:
        allow access to the skin of the user's wrist for a sampler; and
        receive the sampling needle and pass the sampling needle through the second opening to the skin of the user's wrist;
    a processor configured to:
        receive a first plurality of radial pulse intensities from the first plurality of pulse sensors, each radial pulse intensity from the first plurality of radial pulse intensities associated with a respective pulse sensor from the first plurality of pulse sensors;
        determine a highest radial pulse intensity among the first plurality of radial pulse intensities;
        turn on a light from the first plurality of lights associated with the highest pulse intensity among the first plurality of radial pulse intensities;
        receive a second plurality of radial pulse intensities from the second plurality of pulse sensors, each respective radial pulse intensity from the second plurality of radial pulse intensities associated with a respective pulse sensor from the second plurality of pulse sensors;

determine a highest radial pulse intensity among the second plurality of radial pulse intensities;
turn on a light from the second plurality of lights associated with the highest radial pulse intensity among the second plurality of radial pulse intensities;
receive a third plurality of radial pulse intensities from the third plurality of pulse sensors, each respective radial pulse intensity from the third plurality of radial pulse intensities associated with a respective pulse sensor from the third plurality of pulse sensors;
determine a highest radial pulse intensity among the third plurality of radial pulse intensities; and
turn on a light from the third plurality of lights associated with the highest radial pulse intensity among the third plurality of radial pulse intensities;
a wrist gripping member configured to:
receive the user's wrist; and
hold and secure the user's wrist in a predetermined position, the wrist gripping member comprising:
a cushion part configured to receive and hold a forearm of the user; and
an inclined hand holding part, a proximal end of the inclined hand holding part attached to a distal end of the cushion part, the inclined hand holding part configured to receive and hold a hand of the user, the cushion part and the inclined hand holding part forming an angle between the cushion part and the inclined hand holding part, the angle between 120° and 160°;
a first wristlet band attached to a first end of the main part;
a second wristlet band attached to a second end of the main part, the first wristlet band and the second wristlet band configured to secure the main part on the palm side of the user's wrist; and
a hand gripping band attached to a back side of the inclined hand holding part, the hand gripping band configured to secure the hand of the user on the inclined hand holding part.

2. A system for facilitating arterial blood gas (ABG) sampling, the system comprising:
a main part configured to be secured on a palm side of a user's wrist;
a first plurality of pulse sensors attached in a row on an inner surface of the main part, each pulse sensor from the first plurality of pulse sensors configured to measure an intensity of radial pulse around the each pulse sensor, the first plurality of pulse sensors equally spaced on the inner surface of the main part, a distance between centers of each two consecutive pulse sensors from the first plurality of pulse sensors being 5 mm;
a first plurality of lights attached in a row on an external surface of the main part, each respective light from the first plurality of lights associated with a respective pulse sensor from the first plurality of pulse sensors, each light from the first plurality of lights placed behind a respective pulse sensor from the first plurality of pulse sensors, the first plurality of lights equally spaced on the external surface of the main part, a distance between centers of each two consecutive lights from the first plurality of lights being 5 mm;
a second plurality of pulse sensors attached in a row on the internal surface of the main part, each pulse sensor from the second plurality of pulse sensors configured to measure an intensity of radial pulse around each respective pulse sensor, the second plurality of pulse sensors equally spaced on the inner surface of the main part, a distance between centers of each two consecutive pulse sensors from the second plurality of pulse sensors being 5 mm;
a second plurality of lights attached in a row on the external surface of the main part, each respective light from the second plurality of lights associated with a respective pulse sensor from the second plurality of pulse sensors, each light from the second plurality of lights placed behind a respective pulse sensor from the second plurality of pulse sensors, the second plurality of lights equally spaced on the external surface of the main part, a distance between centers of each two consecutive lights from the second plurality of lights being 5 mm;
a third plurality of pulse sensors attached in a row on the internal surface of the main part, each pulse sensor from the third plurality of pulse sensors configured to measure an intensity of radial pulse around the each pulse sensor, the third plurality of pulse sensors equally spaced on the inner surface of the main part, a distance between centers of each two consecutive pulse sensors from the third plurality of pulse sensors being 5 mm;
a third plurality of lights attached in a row on the external surface of the main part, each respective light from the third plurality of lights associated with a respective pulse sensor from the second plurality of pulse sensors, each light from the third plurality of lights placed behind a respective pulse sensor from the third plurality of pulse sensors, the third plurality of lights equally spaced on the external surface of the main part, a distance between centers of each two consecutive lights from the third plurality of lights being 5 mm;
a first opening on the main part adjacent to the first plurality of pulse sensors, the first opening placed between the first plurality of pulse sensors and the second plurality of pulse sensors, a first light from the first plurality of lights placed adjacent to a first end of the first opening, a second light from the first plurality of lights placed adjacent to a second end of the first opening, a width of the first opening being 4 mm, the first opening configured to:
allow access to a skin of the user's wrist for a sampler; and
receive a sampling needle and pass the sampling needle through the first opening to the skin of the user's wrist;
a second opening on the main part between the second plurality of pulse sensors and the third plurality of pulse sensors, a first light from the second plurality of lights placed adjacent to the first end of the first opening and a first end of the second opening, a second light from the second plurality of lights placed adjacent to the second end of the first opening and a second end of the second opening, a first light from the third plurality of lights placed adjacent to the first end of the second opening, a second light from the third plurality of lights placed adjacent to the second end of the second opening, a width of the second opening being 4 mm, the second opening configured to:
allow access to the skin of the user's wrist for a sampler; and
receive the sampling needle and pass the sampling needle through the second opening to the skin of the user's wrist;
a processor configured to:
receive a first plurality of radial pulse intensities from the first plurality of pulse sensors, each radial pulse intensity from the first plurality of radial pulse intensities associated with a respective pulse sensor from the first plurality of pulse sensors;
determine a highest radial pulse intensity among the first plurality of radial pulse intensities;
turn on a light from the first plurality of lights associated with the highest pulse intensity among the first plurality of radial pulse intensities;
receive a second plurality of radial pulse intensities from the second plurality of pulse sensors, each respective radial pulse intensity from the second plurality of radial pulse intensities associated with a respective pulse sensor from the second plurality of pulse sensors;
determine a highest radial pulse intensity among the second plurality of radial pulse intensities;
turn on a light from the second plurality of lights associated with the highest radial pulse intensity among the second plurality of radial pulse intensities;
receive a third plurality of radial pulse intensities from the third plurality of pulse sensors, each respective radial pulse intensity from the third plurality of radial pulse intensities associated with a respective pulse sensor from the third plurality of pulse sensors;
determine a highest radial pulse intensity among the third plurality of radial pulse intensities; and
turn on a light from the third plurality of lights associated with the highest radial pulse intensity among the third plurality of radial pulse intensities;
a wrist gripping member configured to:
  receive the user's wrist; and
  hold and secure the user's wrist in a predetermined position, the wrist gripping member comprising:
    a cushion part configured to receive and hold a forearm of the user; and
    an inclined hand holding part, a proximal end of the inclined hand holding part attached to a distal end of the cushion part, the inclined hand holding part configured to receive and hold a hand of the user, the cushion part and the inclined hand holding part forming an angle between the cushion part and the inclined hand holding part, the angle between 120 and 160;
a first wristlet band attached to a first end of the main part;
a second wristlet band attached to a second end of the main part, the first wristlet band and the second wristlet band configured to secure the main part on the palm side of the user's wrist; and
a hand gripping band attached to a back side of the inclined hand holding part, the hand gripping band configured to secure the hand of the user on the inclined hand holding part.

* * * * *